United States Patent [19] … [11] 4,046,901
Nedelec et al. [45] Sept. 6, 1977

[54] PHENYLPIPERIDINES

[75] Inventors: Lucien Nedèlec, Le Raincy; Jacques Guillaume, Aulnay-sous-Bois; Claude Dumont, Nogent-sur-Marne, all of France

[73] Assignee: Roussel-UCLAF, Paris, France

[21] Appl. No.: 686,076

[22] Filed: May 13, 1976

[30] Foreign Application Priority Data

May 16, 1975    France ........................... 75.15381

[51] Int. Cl.² ................ C07D 211/22; A61K 31/445
[52] U.S. Cl. ............................. 424/267; 260/293.81; 260/293.82; 260/293.83; 260/293.84; 260/295 R; 260/297 R
[58] Field of Search .............. 260/293.81, 293.82, 260/293.83, 293.84, 295 R, 297 R; 71/94; 424/267

[56] References Cited

U.S. PATENT DOCUMENTS 3,954,779   5/1976   Smith et al. .................. 260/293.82

OTHER PUBLICATIONS

Sugimoto et al., J. Pharm. Soc. Japan 75, 183–187 (1955).

Primary Examiner—John M. Ford
Attorney, Agent, or Firm—Hammond & Littell

[57] ABSTRACT

Novel compounds selected from the group consisting of phenylpiperidines of the formula

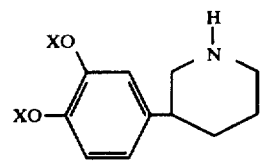

wherein X is selected from the group consisting of hydrogen and an acyl of aliphatic carboxylic acid of 2 to 6 carbon atoms and their non-toxic, pharmaceutically acceptable acid addition salts possessing dopaminergic properties and some of which possess hypotensive properties and their preparation.

11 Claims, No Drawings

PHENYLPIPERIDINES

STATE OF THE ART

J. Pharm. Soc. Japan, Vol. 75 (1955), p. 180–183 describes N-methyl-dimethoxyphenyl-piperidine as an intermediate to prepare compounds having analgesic properties.

OBJECTS OF THE INVENTION

It is an object of the invention to provide the novel phenylpiperidines of formula I and their non-toxic, pharmaceutically acceptable acid addition salts and processes for their preparation as well as novel intermediates.

It is a further object of the invention to provide a novel process for inducing hypotensive activity in warm-blooded animals.

It is another object of the invention to provide novel dopaminergic compositions and a method of treating neurological syndromes of extrapyramidal origin.

These and other objects and advantages of the invention will become obvious from the following detailed description.

THE INVENTION

The novel compounds of the invention are selected from the group consisting of phenylpiperidines of the formula

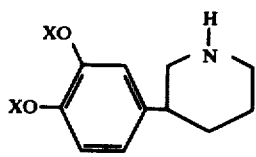

wherein X is selected from the group consisting of hydrogen and an acyl of aliphatic carboxylic acid of 2 to 6 carbon atoms and their non-toxic, pharmaceutically acceptable acid addition salts.

Examples of X are hydrogen and acyl of alkanoic acids of 2 to 6 carbon atoms such as acetic acid, propionic acid, n-butyric acid, isobutyric acid, n-valeric acid and pivalic acid.

The acid addition salts may be derived from organic acids such as acetic acid, formic acid, benzoic acid, maleic acid, fumaric acid, succinic acid, tartaric acid, citric acid, oxalic acid, glyoxylic acid, aspartic acid; alkanesulfonic acids such as methane sulfonic acid; aryl sulfonic acids such as benzene sulfonic acid; and mineral acids such as hydrochloric acid, hydrobromic acid, hydroiodic acid, nitric acid, sulfuric acid or phosphoric acid.

Among the preferred compounds of the invention are those where X is hydrogen or acetyl and their non-toxic, pharmaceutically acceptable acid addition salts. Two specific products are 3-(3′,4′-dihydroxyphenyl)-piperidine hydrobromide and 3-(3′,4′-diacetoxyphenyl)-piperidine oxalate.

The process of the invention for the preparation of a compound of formula I comprises reacting 3,4-dimethoxy-bromo benzene with magnesium in an anhydrous ether to obtain

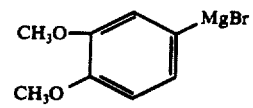

reacting the latter with N-benzyl-3-piperidone to obtain the compound of the formula

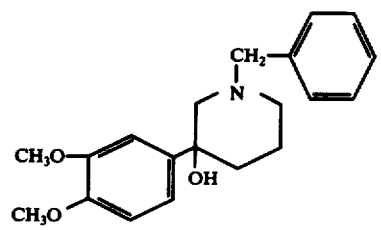

dehydrating the latter with a strong acid to obtain a compound of the formula

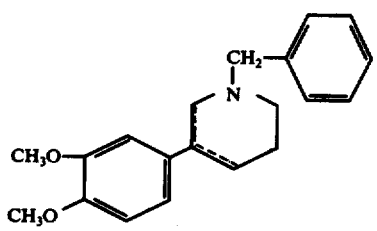

wherein the dotted line indicates a double bond in the 2,3 or 3,4 position of the piperidine group and (a) hydrogenating the latter in the presence of a hydrogenation catalyst in a lower alkanol to obtain a compound of the formula

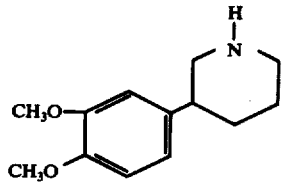

and reacting the latter with hydrobromic acid to form 3-(3′,4′-dihydroxyphenyl)-piperidine hydrobromide which can be treated with a base to form 3-(3′,4′-dihydroxyphenyl)-piperidine or (b) hydrogenating a compound of formula IV in the presence of a catalyst in a lower alkyl acetate to form N-benzyl-3-(3′,4′-dimethoxyphenyl)-piperidine, reacting the latter with hydrobromic acid to obtain N-benzyl-3-(3′,4′-dihydroxyphenyl)-piperidine hydrobromide, reacting the latter with a base to form the corresponding free base which can be salified if desired, reacting the latter products with esterification agent of the formula (X′)$_2$—O or X′-Hal wherein Hal is chlorine or bromine and X′ is an acyl of an aliphatic acid of 2 to 6 carbon atoms to obtain a compound of the formula

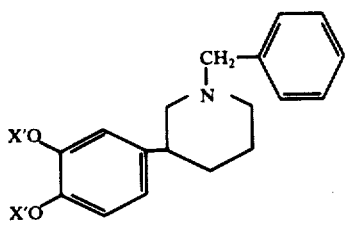

then reducing the salt of the said product with hydrogen in the presence of a catalyst in a lower molecule weight alkanol to obtain a compound of the formula

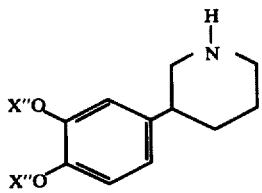

in the form of its acid addition salt which may be treated with a base to form the free base which if desired may be then salified.

In the preferred conditions of the process of the invention, the reaction with 3,4-dimethoxy bromobenzene is effected in an anhydrous ether such as ethyl ether or tetrahydrofuran as well as the reaction of the compound of formula II and N-benzyl-3-piperidone. The dehydration of the compound of formula III is effected with a strong acid such as hydrochloric acid at the reflux of the reaction mixture.

The reduction of the compound of formula IV may be effected with hydrogen in the presence of a catalyst such as palladium or palladium hydroxide either in the presence of a lower alkanol such as methanol, ethanol or propanol or in the presence of a lower alkyl acetate such as ethyl acetate. The reduction of the compound of formula VI is effected with hydrogen in the presence of a catalyst such as palladium or palladium hydroxide in the presence of a lower alkanol such as methanol, ethanol or propanol. The acid addition salts of formula I may be prepared by reaction of stoichiometric amounts of the acid and the free base. The hydrobromide salt is advantageously formed without isolation of the corresponding base.

In a variation of the process of the invention, a bromobenzene of the formula

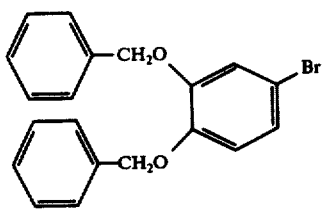

is reacted with magnesium in an anhydrous ether to obtain a compound of the formula

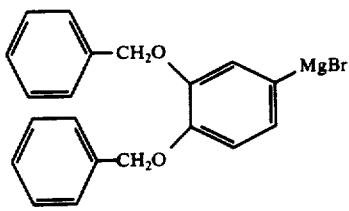

reacting the latter with N-benzyl-3-piperidone to obtain a compound of the formula

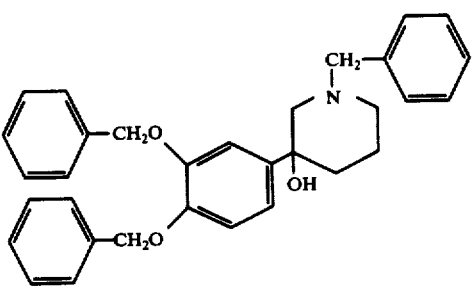

dehydrating the latter with a strong acid to form a compound of the formula

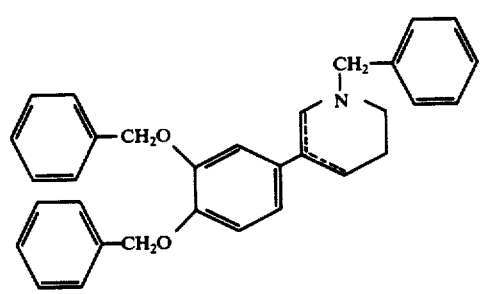

wherein the dotted lines represents a double bond in the 2,3 or 3,4- of piperidine and reducing the latter with hydrogen in the presence of a catalyst and in a lower alkanol to obtain 3-(3',4'-dihydroxyphenyl)-piperidine which can be salified, if desired.

The preferred reaction conditions for the said variation is effecting the reaction with magnesium in an anhydrous ether such as tetrahydrofuran or ethyl ether and the next reaction step is also effected in the said solvent. The dehydration is effected with a strong acid such as hydrochloric acid at reflux and the reduction with hydrogen is effected with a palladium or palladium hydroxide catalyst in a lower alkanol such as methanol, ethanol or propanol.

The novel dopaminergic compositions of the invention are comprised of an effective amount of at least one compound of formula I and their non-toxic, pharmaceutically acceptable acid addition salts and an inert pharmaceutical carrier. The compositions may be in the form of tablets, dragees, gelules, granules, capsules, suppositories, and injectable solutions or suspensions prepared in the usual manner.

Examples of excipients or pharmaceutical carriers are talc, gum arabic, lactose, starch, magnesium stearate, cacao butter, aqueous and non-aqueous vehicles, fatty bodies of animal or vegetable origin, paraffinic derivatives, glycols, preservatives and diverse wetting agents, dispersants or emulsifiers.

The compositions are useful for treatment of Parkinson disease, for the treatment of post-encephalitic Parkinson syndromes, of Parkinson syndromes of arteriosclerous origin or toxic etiology. Certain of the compounds, notably 3-(3',4'-dihydroxyphenyl)-piperidine and its non-toxic, pharmaceutically acceptable acid addition salts, possess hypotensive activity and are useful for the treatment of hypertension.

The preferred compositions are those where X is hydrogen or acetyl and their acid addition salts. Specific preferred compositions are those containing 3-(3',4'-dihydroxyphenyl)-piperidine hydrobromide and 3-(3',4'-diacetoxyphenyl)-piperidine oxalate.

The novel method of the invention for the treatment of the symptoms of Parkinson disease comprises administering to humans an effective amount of at least one compound of formula I and their non-toxic, pharmaceutically acceptable acid addition salts. The products may be administered either orally, rectally or parenterally and the usual daily dose is 0.2 to 20 mg/kg.

The novel method of treating hypertension in warm-blooded animals, including humans, comprising administering to warm-blooded animals an hypotensively effective amount of 3-(3',4'-dihydroxyphenyl)-piperidine and its non-toxic, pharmaceutically acceptable acid addition salts. The novel effective dose is 0.2 to 20 mg/kg.

The novel intermediate products of the invention are compounds of the formula

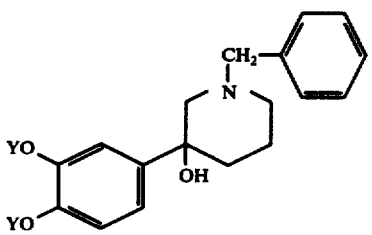

wherein Y is –CH₃ or benzyl, compounds of the formula

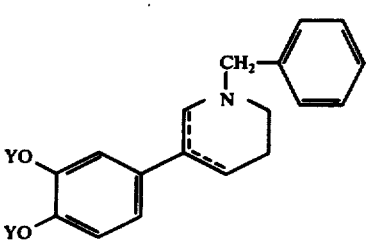

wherein Y is –CH₃ or benzyl and the dotted line represents a double bond in the 2,3 or 3,4- position of the piperidine ring and N-benzyl-3-(3',4'-dimethoxyphenyl)-piperidine.

In the following examples there are described several preferred embodiments to illustrate the invention. However, it should be understood that the invention is not intended to be limited to the specific embodiments.

EXAMPLE 1

3-(3',4'-dihydroxyphenyl)-piperidine hydrobromide

STEP A:

N-benzyl-3-(3',4'-dimethoxyphenyl)-3-hydroxy-piperidine

A few drops of a solution of 75 g of 1-bromo-3,4-dimethoxy-benzene in 110 ml of tetrahydrofuran and an iodine crystal were added to 8.25 g of magnesium in 40 ml of tetrahydrofuran and the mixture was slightly heated. The rest of the solution of the above brominated compound was added at reflux which was maintained for an hour after which the solution was cooled to 20° C.

A solution of 20 g of N-benzyl-3-piperidone in 100 ml of tetrahydrofuran was slowly added with cooling to a 150 ml of the preceding solution and the mixture was stirred at 20° C for 1 hour and then at 50° C for 2 hours. The mixture was cooled and 250 ml of an aqueous solution saturated with ammonium chloride was slowly added. The mixture was extracted with ethyl acetate and the extracts were dried and evaporated to dryness. The residue was taken up in ethyl acetate and the solution was extracted with 2N hydrochloric acid. The acid extracts were made alkaline with sodium hydroxide and were extracted with ethyl acetate. The extracts were dried and evaporated to dryness and the residue was chromatographed over silica gel. Elution with an 85-10-5 cyclohexane-chloroform-triethylamine yielded 27.8 g of N-benzyl-3-(3',4'-dimethoxyphenyl)-3-hydroxy-piperidine.

STEP B:

N-benzyl-3-(3',4'-dimethoxyphenyl)-1,2,5,6-(and 1,4,5,6)-tetrahydropyridine

A mixture of 2 g of N-benzyl-3-(3',4'-dimethoxyphenyl)-3-hydroxy-piperidine and 20 ml of 2N hydrochloric acid was refluxed for 2 hours and was poured over ice. The mixture was made alkaline with sodium hydroxide and was extracted with methylene chloride. The extracts were dried and evaporated to dryness to obtain 1.76 g of a mixture of $\Delta^{2,3}$ and $\Delta^{3,4}$ isomers of N-benzyl-3-(3',4'-dimethoxyphenyl)-tetrahydropyridine. Chromatography of the product over silica gel and elution with an 85-10-5 cyclohexane-chloroform-triethylamine mixture yielded 0.66 g of the $\Delta^{3,4}$-isomer and 0.92 g of the $\Delta^{2,3}$-isomer.

STEP C: 3-(3',4'-dimethoxyphenyl)-piperidine hydrochloride

A mixture of 900 mg of 10 percent palladized activated carbon in 36 ml of ethanol was placed under a hydrogen atmosphere and 1.8 g of the $\Delta^{2,3}$ and $\Delta^{3,4}$ isomers of Step B were added thereto. The hydrogenation was continued until hydrogen adsorption ceased and the mixture was filtered to remove the catalyst. The filtrate was evaporated to dryness and the residue was dissolved in ethyl acetate. The solution was acidified with a saturated hydrochloric acid in ethyl acetate solution and the mixture was vacuum filtered to obtain 1.2 g of 3-(3',4'-dimethoxyphenyl)-piperidine hydrochloride melting at 216° C.

| | Analysis: $C_{13}H_{20}ClNO_2$ | | | |
|---|---|---|---|---|
| Calculated: | %C 60.57 | %H 7.82 | %Cl 13.76 | %N 5.43 |
| Found: | 60.5 | 7.9 | 13.6 | 5.5 |

STEP D: 3-(3',4'-dihydroxyphenyl)-piperidine hydrobromide

A solution of 5 g of the hydrochloride of Step C in 25 ml of 66% hydrobromic acid was heated at 115° C for an hour and excess hydrobromic acid was removed under reduced pressure. The residue was empasted with ethyl acetate and was crystallized from ethanol to obtain 3.85 g of 3-(3',4'-dihydroxyphenyl)-piperidine hydrobromide melting at 224° C.

| | Analysis: $C_{11}H_{16}BrNO_2$ | | | |
|---|---|---|---|---|
| Calculated: | %C 48.19 | %H 5.88 | %Br 29.15 | %N 5.11 |
| Found: | 47.9 | 6.1 | 28.9 | 5.0 |

EXAMPLE 2

3-(3',4'-dihydroxyphenyl)-piperidine hydrobromide

STEP A:
N-benzyl-3-(3',4'-dibenzyloxyphenyl)-3-hydroxy-piperidine

Using the procedure of J. Org. Chem., Vol. 33 (1968), p. 1760, a mixture of 535 mg of magnesium and a few iodine crystals was heated so that the iodine sublinated and after cooling the mixture, 10 ml of tetrahydrofuran, a few drops of a solution of 7.6 g of 1-bromo-3,4-dibenzyloxy benzene in 10 ml of tetrahydrofuran and then a few drops of methyl magnesium iodide prepared extemporaneously were added thereto. Then the rest of the 1-bromo-3,4-dibenzyloxy benzene solution was slowly added at reflux and the mixture was then refluxed for 2 hours and cooled to 20° C to obtain a solution titrating 0.65 M of magnesian.

A solution of 0.85 g of N-benzyl-3-piperidone in 10 ml of tetrahydrofuran was slowly added at 20° C to 10 ml of the previously prepared solution and the mixture was stirred for 20 hours. 20 ml of water were slowly added to the mixture which was then filtered and the precipitate was washed with ethyl acetate. The filtrate was dried and evaporated to dryness and the residue was chromatographed over silica gel. Elution with a 90-5-5 cyclohexane-chloroform-triethyl-amine mixture yielded 1.43 g of N-benzyl-3-(3',4'-dibenzyloxyphenyl)-3-hydroxy-piperidine melting at 80° C.

STEP B:
N-benzyl-3-(3',4'-dibenzyloxyphenyl)-1,2,5,6-tetrahydropyridine

A mixture of 1.5 g of the product of Step A in 15 ml of 2N hydrochloric acid was refluxed for 6 hours and after cooling, the mixture was diluted with methylene chloride. The mixture was made alkaline with sodium hydroxide addition and the methylene chloride phase was recovered by decanting, was dried and evaporated to dryness. The residue was chromatographed over silica gel and elution with a 90-5-5 cyclohexane-chloroform-triethylamine mixture yielded 0.76 g of N-benzyl-3-(3',4'-dibenzyloxyphenyl)-1,2,5,6-tetrahydropyridine.

STEP C: 3-(3',4'-dihydroxyphenyl)-piperidine hydrobromide

A solution of 750 mg of the product of Step B in 30 ml of methanol was mixed with 375 mg of activated carbon containing 10% palladium and the mixture was hydrogenated until hydrogen absorption ceased. The mixture was filtered to remove the catalyst and the filtrate was evaporated to dryness. The residue was dissolved in ethanol and after cooling, hydrobromic acid was bubbled therethrough until the solution was saturated. The mixture was vacuum filtered and the recovered precipitate was washed with ethanol and dried to obtain 135 mg of 3-(3',4'-dihydroxyphenyl)-piperidine hydrobromide melting at 224° C.

EXAMPLE 3

3-(3',4'-diacetoxyphenyl)-piperidine oxalate

STEP A:
N-benzyl-3-(3',4'-dimethoxyphenyl)-piperidine 2.5 g of 10% palladized activated carbon were added to a solution of 5 g of the mixture of $\Delta^{2,3}$ and $\Delta^{3,4}$-isomers from Step B of Example 1 in 200 ml of ethyl acetate and hydrogen was introduced until the theoretical amount of hydrogen absorption was reached. The catalyst was removed by filtration and the filtrate was evaporated to dryness. The residue was chromatographed over silica gel and elution with an 85-10-5 cyclohexane-chloroform-triethylamine mixture yielded 2.7 g of N-benzyl-3-(3',4'-dimethoxyphenyl)-piperidine.

STEP B: N-benzyl-3-(3',4-dihydroxyphenyl)-piperidine oxalate

A mixture of 5.25 g of the product of Step A in 53 ml of 66% hydrobromic acid was refluxed for an hour and the mixture was distilled to dryness under reduced pressure. The residue was taken up in water and methylene chloride was added thereto. The mixture was made alkaline with sodium bicarbonate and the methylene chloride phase was recovered by decanting, was dried and evaporated to dryness. The residue was dissolved in 50 ml of isopropanol and a solution of 1 g of oxalic acid in 30 ml of isopropanol was added thereto. The mixture was heated to reflux and after crystallization, was cooled and vacuum filtered. The recovered crystals were dried to obtain 4.9 g of N-benzyl-3-(3',4'-dihydroxyphenyl)-piperidine oxalate melting at 208° C.

| | Analysis: $C_{19}H_{22}NO_4$ | | |
|---|---|---|---|
| Calculated: | %C 69.49 | %H 6.75 | %N 4.27 |
| Found: | 69.4 | 6.6 | 4.1 |

STEP C: N-benzyl-3-(3',4'-diacetoxyphenyl)-piperidine oxalate 9.8 g of anhydrous sodium acetate were added to a mixture of 9.8 g of the product of Step B and 120 ml of acetic acid anhydride and the mixture was stirred at 20° C for 3 hours and was then filtered. The filter was washed with ethanol and the filtrate was evaporated to dryness under reduced pressure. The residue was taken up in water and ethyl acetate and the solution was made alkaline with an aqueous solution saturated with sodium bicarbonate. The ethyl acetate phase was recovered by decanting, was dried and evaporated to dryness. The residue was dissolved in 50 ml of isopropanol and a solution of 4 g of oxalic acid in 50 ml of isopropanol was added thereto. The mixture was refluxed until dissolution occurred and was cooled to 20° C and vacuum filtered to obtain 13.5 g of N-benzyl-3-(3',4'-diacetoxyphenyl)-piperidine oxalate melting at 145° C.

|  | Analysis: $C_{24}H_{27}NO_8$ | | |
|---|---|---|---|
| Calculated: | %C 63.01 | %H 5.95 | %N 3.06 |
| Found: | 63.0 | 6.0 | 3.0 |

STEP D: 3-(3',4'-diacetoxyphenyl)-piperidine oxalate 5 g of 10% palladized activated carbon were added to a solution of 10 g of the product of Step C in 600 ml of ethanol and hydrogen was introduced until hydrogen absorption ceased. The mixture was filtered and the filtrate was evaporated to dryness. The residue was dissolved in ethanol and the solution was cooled and vacuum filtered. The mother liquors were concentrated while progressively adding ethanol to a volume of 50 ml and was cooled and vacuum filtered. The recovered crystals were dried to obtain 3.25 g of 3-(3',4'-diacetoxyphenyl)-piperidine oxalate melting at 160° C.

|  | Analysis: $C_{17}H_{21}NO_8$ | | |
|---|---|---|---|
| Calculated: | %C 55.58 | %H 5.76 | %N 3.81 |
| Found: | 55.5 | 6.0 | 3.8 |

EXAMPLE 4

Tablets were prepared containing 50 mg of 3-(3',4'-dihydroxyphenyl)-piperidine hydrobromide or 50 mg of 3-(3',4'-diacetoxyphenyl)-piperidine oxalate and a sufficient amount of an excipient consisting of lactose, starch, talc and magnesium stearate to obtain a final weight of 150 mg.

PHARMACOLOGICAL DATA

A. Antagonism Against Reserpinic Rigidity

The antagonism of the test products against reserpinic rigidity was determined on rats using the procedure of Jurna I: Arch. Pharmak. Exp. Path., Vol. 260 (1968), p. 80-88 and the electromyogram (EMG) provoked by a dorsiflexion of the instep was determined with electrodes placed against the muscles in the front loge of a rear foot of the animal. A dose of 10 mg/kg of reserpine was administered intraveinously and 30 minutes later when the muscle hypertonicity was greatest, the test product was administered intraveinously at a dose of 2 or 5 mg/kg. The electromyogram responses were determined before and after the administration of the test compound and were compared for their intensity and duration. The inhibition observed by the electromyogram showed antagonism exercised by the test product against the rigidity provoked by resperpine and the results were expressed in an increasing number of + as a function of the dose expressed in mg/kg. The results are reported in Table I.

TABLE I

| Product of Example | Dose in mg/kg | Resperpine antagonism |
|---|---|---|
| 1 | 5 | + + |
| 3 | 2 | + + |

The results of Table I show that the tested products were very active.

B. Behavior After Unilateral Injury Of Nigrostriated Fasciculus

Among the animals having undergone an electrolytic unilateral lesion of nigrostriated fasciculus, the substances having a dopaminergic activity showed a behavior of rotation in the side of the lesion. The test animals were male rats weighing about 250 g and the lesion was effected on the right side at the level of the striatum with an anodic current of 2 mA for a duration of 30 seconds /Anden et al, Acta. Pharmacol. Toxicol., Vol. 24 (1966), p. 263-274/. The test compounds were administered intraperitoneally to groups of 6 animals and they were individually placed in a rotometer which counted the number of rotations of each animal in two ways. Each test was continued for 1½ hours. Under these conditions, the products of Examples 1 and 3 showed psi-lateral rotations at a dose of 25 mg/kg which showed that the products possess an important dopaminergic activity.

C. Hypotensive Activity

The hypotensive activity was determined on male rats of the Sprague-Dawley S.P.F. strain weighing about 300 g and anesthesized with nembutal at an intraveinous dose of 50 mg/kg. The test product was administered intraveinously into the jugular vein and the carotidiene pressure was measured before and after the administration of the test compound. The variation in the arterial pressure after the administration of the test compound as compared to the initial arterial pressure as well as the time necessary for the pressure to return to the initial value were determined. Under the test conditions, the product of Example 1 exerted a 20% hypotension for 30 minutes at a dose of 1 mg/kg.

D. Acute Toxicity

The 50% lethal dose ($DL_{50}$) was determined for the products after intraperitoneal administration to mice and the mortality was determined 48 hours after the administration of the test product. The $DL_{50}$ for products of Examples 1 and 3 was about 150 and about 100 mg/kg, respectively.

Various modifications of the products and methods of the invention may be made without departing from the spirit or scope thereof and it is to be understood that the invention is to be limited only as defined in the appended claims.

We claim:

1. A compound selected from the group consisting of phenylpiperidines of the formula

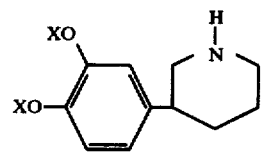

wherein X is selected from the group consisting of hydrogen and an acyl of alkanoic acid of 2 to 6 carbon atoms and their non-toxic, pharmaceutically acceptable acid addition salts.

2. A compound of claim 1 wherein X is selected from the group consisting of hydrogen and acetyl.

3. A compound of claim 1 which is 3-(3',4'-dihydroxyphenyl)-piperidine hydrobromide.

4. A compound of claim 1 which is 3-(3',4'-diacetoxyphenyl)-piperidine oxalate.

5. A compound selected from the group consisting of N-benzyl-3-(3',4'-dimethoxyphenyl)-piperidine, a compound of the formula

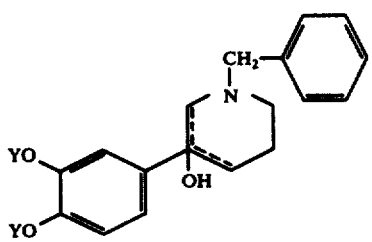

and a compound of the formula

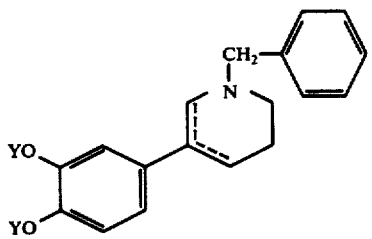

wherein Y is selected from the group consisting of —$CH_3$ and benzyl and the dotted line is a double bond in the 2,3 or 3,4 position of piperidine.

6. A dopaminergic composition comprising a dopaminergically effective amount of at least one compound of claim 1 and an inert pharmaceutical carrier.

7. A method of treating the symptoms of Parkinson disease comprising administering to humans an effective amount of at least one compound of claim 1.

8. The method of claim 7 wherein X is hydrogen or acetyl.

9. The method of claim 7 wherein 3-(3',4'-dihydroxyphenyl)-piperidine hydrobromide is used.

10. The method of claim 7 wherein 3-(3',4'-diacetoxyphenyl)-piperidine oxalate is used.

11. A method of reducing hypertension in warm-blooded animals comprising administering to warm-blooded animals an hypotensively effective amount of 3-(3',4'-dihydroxyphenyl)-piperidine or its non-toxic, pharmaceutically acceptable acid addition salts.

* * * * *